United States Patent
Pugia et al.

(10) Patent No.: US 10,604,751 B2
(45) Date of Patent: Mar. 31, 2020

(54) SELECTIVE NUCLEIC ACID SEPARATION

(71) Applicant: SIEMENS HEALTHCARE DIAGNOSTICS INC., Tarrytown, NY (US)

(72) Inventors: Michael Pugia, Granger, IN (US); Julia Philip, South Bend, IN (US); Karen Marfut, Edwardsburg, MI (US)

(73) Assignee: Siemens Healthcare Disgnostics Inc., Tarrytown, NY (US)

(*) Notice: Subject to any disclaimer, the term of this patent is extended or adjusted under 35 U.S.C. 154(b) by 0 days.

(21) Appl. No.: 15/322,814

(22) PCT Filed: Jul. 2, 2015

(86) PCT No.: PCT/US2015/038990
§ 371 (c)(1),
(2) Date: Dec. 29, 2016

(87) PCT Pub. No.: WO2016/004308
PCT Pub. Date: Jan. 7, 2016

(65) Prior Publication Data
US 2017/0137805 A1    May 18, 2017

Related U.S. Application Data

(60) Provisional application No. 62/020,181, filed on Jul. 2, 2014.

(51) Int. Cl.
*C12N 15/10* (2006.01)
*C12Q 1/6806* (2018.01)
*C12Q 1/6844* (2018.01)

(52) U.S. Cl.
CPC ..... *C12N 15/1017* (2013.01); *C12N 15/1003* (2013.01); *C12N 15/1006* (2013.01); *C12Q 1/6806* (2013.01)

(58) Field of Classification Search
CPC ............ C12N 15/1017; C12N 15/1003; C12Q 1/6806
See application file for complete search history.

(56) References Cited

U.S. PATENT DOCUMENTS

| 2008/0057505 A1 | 3/2008 | Lin et al. |
| 2008/0090239 A1 | 4/2008 | Shoemaker et al. |
| 2010/0209930 A1 | 8/2010 | Fernando |
| 2011/0027771 A1* | 2/2011 | Deng .................. C12Q 1/6806 435/2 |
| 2011/0070642 A1* | 3/2011 | Cayre .................. C12M 47/04 435/325 |
| 2012/0264628 A1 | 10/2012 | Okamoto et al. |
| 2013/0171615 A1* | 7/2013 | Van Meerbergen ..... C12N 1/06 435/2 |
| 2013/0316347 A1 | 11/2013 | Brechot et al. |

FOREIGN PATENT DOCUMENTS

| WO | WO-03018757 A2 * | 3/2003 | ............... A01N 1/00 |
| WO | 03031938 A2 | 4/2003 | |

OTHER PUBLICATIONS

Desitter, I. et al., A New Device for Rapid Isolation by Size and Characterization of Rare Circulating Tumor Cells, Anticancer Res., vol. 31, pp. 427-442 (Year: 2011).*
Fasching, P. A. et al., 4EVER: Assessment of circulating tumor cells with a novel, filtration-based method, in phase IIIb multicenter study for postmenopausal, HER2-negative, estrogen receptor-positive, advanced breast cancer patients, Poster 591, ASCO Meeting, May 31-Jun. 4, 2013.*
Canonico, B. et al., Flow Cytometric Profiles, Biomolecular and Morphological Aspects of Transfixed Leukocytes and Red Cells, Cytometry, Part B, vol. 78, pp. 267-278 (Year: 2010).*
Podenphant Marie et al. "Separation of cancer cells from white blood cells by pinched flow fractionation"; Lab on a Chip, vol. 15, No. 24, Oct. 21, 2015, pp. 4598-4606, XP002769392.
Loberg Robert D. et al "Detection and Isolation of Circulating Tumor Cells in Urologic Cancers: A Review" Neoplasla • vol. 6, No. 4, Jul./Aug. 2004, pp. 302-309; XP055325119.
Millner Lori M. "Circulating Tumor Cells: A Review of Present Methods and the Need to Identify Heterogeneous Phenotypes" Annals of Clinical & Laboratory Science, vol. 43, 110.3, 2013, p. 295 XP055314903; Available online at www.anndinlabsci.org.
PCT Search Report and Written Opinion for International Application No. PCT/US15/38990 dated Sep. 23, 2015, 6 pp.

* cited by examiner

*Primary Examiner* — Teresa E Strzelecka

(57) ABSTRACT

Nucleic acids in non-rare cells in a sample containing non-rare cells and rare cells are selectively released from the non-rare cells. The sample is combined with an aqueous medium, and the combination is held for a period of time and at a temperature for selectively releasing nucleic acids from the non-rare cells but not from the rare cells. The sample is subjected to filtration to separate rare cells from non-rare cells. Rare cells with intact nucleic acids are separated from non-rare cells and nucleic acids from the non-rare cells. Nucleic acids from the rare cells are subjected to one or more identification techniques either with or without extraction of nucleic acids from the rare cells.

18 Claims, No Drawings

SELECTIVE NUCLEIC ACID SEPARATION

BACKGROUND

The invention relates to methods for enriching nucleic acids from rare cells relative to nucleic acids from non-rare cells.

Cell filtration for the separation of cancer cells using a porous matrix is used to sort cells by size and, in most instances, such filtration methods allow for the extraction of cells following separation. Both microfluidic post and microfluidic membrane methods are used in these filtration approaches. Rare cells contain only small amounts of nucleic acids and these amounts are well below what can be detected by methods applied prior to separation of rare cells from non-rare cells. Currently, in order to analyze nucleic acids in a sample containing a few rare cells (1 to 1000 cells/10 mL), the nucleic acids must be concentrated. However, this does not increase the purity of the nucleic acids, that is, the ratio of nucleic acids associated with a disease state (disease-associated nucleic acids) to nucleic acids not associated with a disease state (non-disease-associated nucleic acids). Impurities are due to nucleic acids from non-diseased cells, which occur from freely circulating nucleic acids and to nucleic acids from non-rare cells. These impurities make the analysis of nucleic acids from diseased cells insensitive and prone to false results. Therefore, even though methods are known for enhancing an amount of rare cells over non-rare cells, enough of non-disease-associated nucleic acids remain in a sample such that the amount of disease-associated nucleic acids cannot be accurately determined because of the non-disease-associated nucleic acids.

Furthermore, cell filtration typically requires fixation of cells for high recovery of diseased cells. Without fixation, less than 40% recovery of diseased cells is realized whereas with fixation, the recovery is greater than 90%. Fixation is also required for sample stability. However, fixation causes problems as nucleic acids are usually heavily fragmented and chemically modified by a fixation agent such as, for example, formaldehyde. Although formaldehyde modification cannot be detected in standard quality control assays such as, for example, gel electrophoresis, it does strongly interfere with analysis of nucleic acids. While nucleic acid isolation and purification methods can be optimized to reverse as much formaldehyde modification as possible without further RNA degradation, RNA purified from fixed samples is not a good candidate for downstream applications that require full-length RNA such as, for example, polymerase chain reaction methods.

Nucleic acids from rare cells can be found inside rare cells or as circulating nucleic acids free of the cells. Analysis of both cellular and cell free nucleic acids are important. Cellular nucleic acids within rare cells in circulation, such as from circulating tumor cells, are found in patients with cancer. These cells are intact, alive and can often replicate. However the nucleic acids quantities from these cells are of extremely low concentration and in the range of attogram per tube of blood (7-10 mL). This is due the small numbers of these rare cells per tube of blood, for example 1 to 300 circulating tumor cells. However, these cells can survive in blood and cause disease to spread when the cells enter into the tissues of the body. The latency time that these cells can survive in blood is extremely long and on the order of years. Therefore, it is important to know if these diseased rare cells are present and to analyze their nucleic acids to determine whether such cells will adapt and survived the stress of blood with potential to enter tissue or cause a treatment resistant disease.

Cell free nucleic acids arise mainly from rare cells that reside inside tissues, such as rare cells from inside solid cancer tumors and infected tissues. These cell free nucleic acids are released into the circulation in a much higher concentration than nucleic acids from circulating rare cells. The observed range of cell free circulating nucleic acids in blood is between 200 ng to 40 μg per 10 mL of blood in healthy persons. During disease, cell free nucleic acids increased if significant disease is occurring in the tissues. In order to produce nanograms of cell free nucleic acids, billions of rare disease cells must release nucleic acids. Therefore the minimum amount of diseased tissue with rare cells is of significant size, for example a tumor above a critical mass of cm size.

The principle of particle capture is well known and has been used to bind, isolate, separate and concentrate nucleic acids in circulation, such as RNA or DNA (Vogelstein B, Gillespie D., Proc Natl Acad Sci 1979:79:615-19). One of early procedures were developed for removing DNA, involves using glass particles prepared from ground scintillation vials (American Flint Glass Co.). At the time, silica gel and porous glass beads were unsuitable for nucleic acid removal. Recently, silica coated magnetic particles have been found useful to isolate, separate and concentrate nucleic acids, such as RNA or DNA (WO 03/058649, U.S. Pat. Nos. 8,846,897 and 8,703,931). These magnetic particles have a non-porous, ultrathin silica layer and are able to isolate and separate nucleic acids from tissue samples and biological fluids by making use of the silica layer to bind the nucleic acids and the magnetic properties to hold particles during wash steps. The methods are non-selective and capture all nucleic acids whether from rare cells or non-rare cells.

The problem of purity of nucleic acids is exacerbated by methods of isolating nucleic acids. Such methods employ reagents such as, for example, detergents or phenols, which can damage the nucleic acid material. Furthermore, contamination of nucleic acids with other reagents such as organic solvents and other extraction chemicals can affect the integrity of nucleic acid samples. Other integrity problems include degradation, fragmentation, and binding and crosslinking of nucleic acids.

There is, therefore, a need to develop a method of enriching disease-associated nucleic acids over non-disease-associated nucleic acids. The method should improve nucleic acid recovery from rare cells and reduce or eliminate contamination and allow for sensitive and accurate determination of nucleic acids in rare cells.

SUMMARY

Some examples in accordance with the principles described herein are directed to methods of separating rare cells with intact nucleic acids from non-rare cells in a sample comprising the rare cells and non-rare cells. The sample is combined with an aqueous medium, and the combination is held for a period of time and at a temperature for selectively releasing nucleic acids from the non-rare cells but not from the rare cells. The sample is subjected to filtration to separate rare cells from non-rare cells.

Some examples in accordance with the principles described herein are directed to methods of isolating intact nucleic acids from rare cells in a sample comprising the rare cells and non-rare cells. The sample is combined with an aqueous medium, and the combination is held for a period of time and at a temperature for selectively releasing nucleic acids from the non-rare cells but not from the rare cells. The sample is subjected to filtration to separate rare cells from non-rare cells. Intact nucleic acids are extracted from the separated rare cells.

Some examples in accordance with the principles described herein are directed to methods of determining nucleic acids in rare cells in a sample comprising rare cells and non-rare cells. In the method, the sample is combined with an aqueous medium. The combination is held for a period of time and at a temperature for selectively releasing nucleic acids from the non-rare cells but not from the rare cells. The sample is subjected to filtration to separate rare cells from non-rare cells. One or more of the nucleic acids of the rare cells are removed and identified.

Some examples in accordance with the principles described herein are directed to methods of isolating and, optionally, determining cellular and circulating nucleic acids secreted from rare cells into a bodily fluid and free from cells. In the method, the sample is combined with an aqueous medium and nucleic acid capture particles. The combination is held for a period of time and at a temperature for selectively releasing nucleic acids from the non-rare cells but not from the nucleic acid capture particle. The combination is subjected to filtration to separate nucleic acids on the capture particle from other circulating components. One or more of the nucleic acids from capture particles or rare cells are removed and, optionally, identified.

DETAILED DESCRIPTION OF SPECIFIC EMBODIMENTS

Examples in accordance with the principles described herein permit preferential release of nucleic acids from non-rare cells in the presence of rare cells in a sample that contains both non-rare cells and rare cells. Rare cells then can be subjected to one or more identification techniques to identify the nucleic acids present in the rare cells. In some examples, nucleic acids can be extracted from the rare cells prior to identification.

As mentioned above, some examples in accordance with the principles described herein are directed to methods of selectively releasing nucleic acids from non-rare cells in a sample containing non-rare cells and rare cells. The sample to be analyzed is one that is suspected of containing non-rare cells and rare cells. The samples may be biological samples or non-biological samples. Biological samples may be from a mammalian subject or a non-mammalian subject. Mammalian subjects may be, e.g., humans or other animal species. Biological samples include biological fluids such as whole blood, serum, plasma, sputum, lymphatic fluid, semen, vaginal mucus, feces, urine, spinal fluid, saliva, stool, cerebral spinal fluid, tears, and mucus, for example. Biological tissue includes, by way of illustration, hair, skin, sections or excised tissues from organs or other body parts, for example. In many instances, the sample is whole blood, plasma or serum.

Some examples in accordance with the principles described herein are directed to methods of isolating intact nucleic acids from rare cells in a sample comprising the rare cells and non-rare cells. The sample is combined with an aqueous medium, and the combination is held for a period of time and at a temperature for selectively releasing nucleic acids from the non-rare cells but not from the rare cells. The sample is subjected to filtration to separate rare cells from non-rare cells. Intact nucleic acids are extracted from the separated rare cells.

Rare cells are those cells that are present in a sample in relatively small quantities when compared to the amount of non-rare cells in a sample. In some examples, the rare cells are present in an amount of about $10^{-8}\%$ to about $10^{-2}\%$ by weight of a total cell population in a sample suspected of containing the rare cells. The rare cells may be, but are not limited to, malignant cells such as malignant neoplasms or cancer cells; circulating endothelial cells; circulating epithelial cells; fetal cells; immune cells (B cells, T cells, macrophages, NK cells, monocytes); rare immune cells; infective cells; stem cells; nucleated red blood cells (normoblasts or erythroblasts); and immature granulocytes; for example.

Non-rare cells are those cells that are present in relatively large amounts when compared to the amount of rare cells in a sample. In some examples, the non-rare cells are at least about 10 times, or at least about $10^2$ times, or at least about $10^3$ times, or at least about $10^4$ times, or at least about $10^5$ times, or at least about $10^6$ times, or at least about $10^7$ times, or at least about $10^8$ times greater than the amount of the rare cells in the total cell population in a sample suspected of containing non-rare cells and rare cells. The non-rare cells may be, but are not limited to, white blood cells, platelets, and red blood cells, for example.

Cell free nucleic acids arise mainly from rare cells that reside inside tissues, such as rare cells from inside solid cancer tumors and infected tissues. In some examples, cell free nucleic acids are at least about $10^4$ times, or at least about $10^5$ times, or at least about $10^6$ times, or at least about $10^7$ times, or at least about $10^8$ times, or at least about $10^9$ times, or at least about $10^{10}$ times greater than the cellular nucleic acids arising from rare cells in circulation. The cell free nucleic acids may be, for example, DNA or RNA, and may originate from cell nucleus, ribosomes, mitochondrial, cytoplasm and be inside cells, vesicles, exosomes or be freely circulating or circulating in bound forms.

As mentioned above, in some examples the sample to be tested is a blood sample from a mammal such as, but not limited to, a human subject, for example. The blood sample is one that contains cells such as, for example, non-rare cells and rare cells. In some examples the blood sample is whole blood or plasma.

Blood samples are collected from the body of a subject into a suitable container such as, but not limited to, a bag, a bottle, a needle or a VACUTAINER® container, for example. The container may contain a collection medium into which the sample is delivered. The collection medium is usually a dry medium and may comprise an amount of platelet deactivation agent effective to achieve deactivation of platelets in the blood sample when mixed with the blood sample and/or an effective amount of an anticoagulant. The collection medium may also contain one or more additional agents such as, but not limited to, $CrCl_3$ or $MnCl_2$, dextrose, glucose, citrate, adenosine triphosphate, inosine, dihydroxyacetone, 2,3-diphosphoglycerol, chloramphenicol, neomycin sulphate, magnesium chloride, iodoacetamide, sodium ascorbate, acetic acid, dimethylsulfoxide, zinc sulfate, 2-bromo-2-nitropropane-1,3-diol, urea and urea derivatives, acetamide, formamide, hydantoin, alcohols, acetic acid, formic acid, dehydrated oxidant (osmium), fixation agents, growth factors, transferrin inhibitors, and inhibitors for phosphorylation and other enzymes, for example. These additional agents, if present, are present in amounts that achieve their respective intended purposes. In some examples the collection medium is a standard blood collection or anti-coagulant medium. It is important to note that methods in accordance with the principles described herein are effective when fixation agents are not employed, thus avoiding problems in nucleic acid determinations when fixation agents are employed.

Prior to subjecting a sample to methods in accordance with the principles described herein, the sample may be stored for a period of about 12 hours to about 5 days or more at a temperature of about 2° C. to about 40° C., or about 2° C. to 30° C., or about 2° C. to about 20° C., or about 5° C. to about 40° C., or about 5° C. to about 30° C., or about 5° C. to about 25° C., or about 5° C. to about 20° C., or 1° C. to about 40° C., or about 10° C. to about 30° C., or about 10° C. to about 25° C., or about 10° C. to about 20° C., for example.

As mentioned above, in accordance with the principles described herein, the sample is combined with an aqueous medium. The aqueous medium may be solely water or the aqueous medium may also contain organic solvents such as, for example, polar aprotic solvents, polar protic solvents such as, e.g., dimethylsulfoxide (DMSO), dimethylformamide (DMF), acetonitrile, an organic acid, or an alcohol, and non-polar solvents miscible with water such as, e.g., dioxene, in an amount of about 0.1% to about 50%, or about 1% to about 50%, or about 5% to about 50%, or about 1% to about 40%, or about 1% to about 30%, or about 1% to about 20%, or about 1% to about 10%, or about 5% to about 40%, or about 5% to about 30%, or about 5% to about 20%, or about 5% to about 10%, by volume. In some examples, the pH for the aqueous medium is usually a moderate pH. In some examples the pH of the aqueous medium is about 5 to about 8, or about 6 to about 8, or about 7 to about 8, or about 5 to about 7, or about 6 to about 7, or physiological pH, for example.

An amount of aqueous medium employed is dependent on a number of factors such as, but not limited to, the nature and amount of the sample, the nature and amount of any buffer, the pH of the medium, the components of the aqueous medium such as, for example, presence of an organic solvent, the ionic strength of the medium, and the surface tension of the medium, for example. In some examples in accordance with the principles described herein, the amount of aqueous medium per 10 mL of sample is about 5 mL to about 100 mL, or about 5 mL to about 80 mL, or about 5 mL to about 60 mL, or about 5 mL to about 50 mL, or about 5 mL to about 30 mL, or about 5 mL to about 20 mL, or about 5 mL to about 10 mL, or about 10 mL to about 100 mL, or about 10 mL to about 80 mL, or about 10 mL to about 60 mL, or about 10 mL to about 50 mL, or about 10 mL to about 30 mL, or about 10 mL to about 20 mL, or about 20 mL to about 100 mL, or about 20 mL to about 80 mL, or about 20 mL to about 60 mL, or about 20 mL to about 50 mL, or about 20 mL to about 30 mL, for example.

In accordance with the principles described herein, the combination comprising the sample and the aqueous medium is held for a period of time and at a temperature for releasing nucleic acids from the non-rare cells but not from the rare cells. The temperature and duration of this treatment is dependent on the nature of the aqueous medium, the nature of the sample, the nature of any buffer if present, the nature of the rare cells, the nature of the non-rare cells, and the nature of the nucleic acids, for example. In some examples the temperature of the aqueous medium during the holding is about 5° C. to about 40° C., or about 5° C. to about 35° C., or about 5° C. to about 30° C., or about 5° C. to about 25° C., or about 5° C. to about 20° C., or about 5° C. to about 15° C., or about 10° C. to about 30° C., or about 10° C. to about 25° C., or about 10° C. to about 20° C., or about 20° C. to about 25° C., for example. The time period for the treatment of the sample in the aqueous medium is about 15 minutes to about 20 days, or about 15 minutes to about 15 days, or about 15 minutes to about 10 days, or about 15 minutes to about 7 days, or about 15 minutes to about 5 days, or about 1 day to about 20 days, or about 1 day to about 15 days, or about 1 day to about 10 days, or about 1 day to about 5 days, or about 2 days to about 20 days, or about 2 days to about 15 days, or about 2 days to about 10 days, or about 2 days to about 5 days, or about 5 days to about 10 days, or about 10 days to about 20 days, or about 10 days to about 15 days, for example.

In some examples, the aqueous medium comprises a buffer, which may be, but is not limited to, a phosphate buffer (e.g., phosphate buffered saline, monohydrogen phosphate buffer, dihydrogen phosphate buffer; organophosphate buffer (e.g., glycerol phosphate buffer, phenyl phosphate buffer, phytic acid buffer, and alkyl phosphate buffers, or combinations thereof); a carbonate buffer (e.g., a bicarbonate buffer, calcium carbonate and sodium carbonate, or combinations thereof); a carboxylic acid buffer (e.g., citric acid, malic acid, EDTA, alkyl carboxylic acids (e.g., acetic acid); a guanidine (e.g., arginine, creatine, saxitoxin, triazabicyclodecene, guanidine); a borate buffer (e.g., sodium borate buffer or borate buffered saline, or combinations thereof); an XH-substituted aliphatic amine containing 2 to 20 carbon atoms wherein X is O, S or $SO_3$; or barbital, for example, and combinations of two or more of the above.

As mentioned above, in some examples, the buffer is an XH-substituted aliphatic amine containing 2 to 20 carbon atoms wherein X is O, S or $SO_3$. In some examples, the number of carbon atoms in the XH-substituted aliphatic amine is 2 to 15, or 2 to 10, or 2 to 5, or 3 to 15, or 3 to 10, or 3 to 5, or 4 to 20, or 4 to 15, or 4 to 10, or 4 to 5, or 5 to 20, or 5 to 15, or 5 to 10, for example. In some examples the XH-substituted aliphatic amine comprises at least one XH substituent per seven carbon atoms, or at least two XH substituents per seven carbon atoms, or at least three XH substituents per seven carbon atoms, for example. In some examples, the number of XH substituents in the XH-substituted aliphatic amine is 1 to 5, or, 1 to 4, or 1 to 3, or 1 to 2, or 2 to 5, or 2 to 4, or 2 to 3, or 3 to 5, or 3 to 4, or 4 to 5. The term "aliphatic" refers to non-aromatic compounds that may be saturated or unsaturated (i.e., contain one or more double bonds, usually non-conjugated double bonds) or may contain one or more rings that are non-aromatic. The aliphatic amines may contain one or more heteroatoms in addition to the nitrogen atoms of the amine groups where the heteroatoms may be selected from the group consisting of oxygen, sulfur, and phosphorus, for example. The amine may be a primary, a secondary or a tertiary amine and may be branched or unbranched and may be part of one or more non-aromatic rings. The aliphatic amines may contain one or more amine groups, such as, for example, one amine group, or two amine groups, or three amine groups, which may each be independently a primary amine, a secondary amine, or a tertiary amine.

In some examples, the XH-substituted aliphatic amine has the formula $NR^1-R^2-(CH_2)_a$-L wherein:

L is $SO_3H$ or $CR^3R^4R^5$ wherein $R^3$, $R^4$, and $R^5$ are independently H or $CH_2XH$ wherein at least one of $R^3$, $R^4$, and $R^5$ is $CH_2XH$;

a is an integer from 0 to 10, or 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, being at least 1 when L is SO$_3$H; and $R^1$ and $R^2$ are independently H, alkyl, or $(CH_2)_bC(O)NR^6R^7$ wherein:

b is an integer from 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10; and $R^6$ and $R^7$ are independently H or alkyl, or wherein $R^1$ and $R^2$ are taken together to form a five membered aliphatic ring, a six membered aliphatic ring or a seven membered aliphatic ring, which may be, by way of illustration and not limitation, a morpholino ring or a piperazine ring.

In some examples, the XH-substituted aliphatic amine has the formula $NR^1R^2$—$(CH_2)_bCR^3R^4R^5$ wherein $R^1$ and $R^2$ are independently H or alkyl; $R^3$, $R^4$, and $R^5$ are independently H or $CH_2XH$ wherein at least one of $R^3$, $R^4$, and $R^5$ is $CH_2XH$; and b (as defined above) is an integer from 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10.

In some examples, the XH-substituted aliphatic amine is selected from the group consisting of:

$NH_2$—$C(CH_2OH)_3$: 2-amino-2-hydroxymethyl-propane-1,3-diol (TRIS); (HO—$(CH_2)_2)_2$—N—$CH_2$—C(O)OH: 2-(Bis(2-hydroxyethyl)amino)acetic acid (BICINE); $HO_3S$—$(CH_2)_2$—NH—$CH_2$—$C(O)NH_2$: 2-(carbamoylmethylamino)ethanesulfonic acid (ACES); $O(CH_2CH_2)_2$N—$(CH_2)_3$—$SO_3H$: 3-morpholinopropane-1-sulfonic acid (MOPS); $O(CH_2CH_2)_2N$—$(CH_2)_2$—$SO_3H$: 2-(N-morpholino)ethanesulfonic acid (MES); HO—$(CH_2)_2$—$N(CH_2CH_2)_2N$—$(CH_2)_2$—$SO_3H$: 2-[4-(2-hydroxyethyl)piperazin-1-yl]-ethanesulfonic acid (HEPES); and $HO_3S$—$(CH_2)_2$—$N(CH_2CH_2)_2N$—$(CH_2)_2$—$SO_3H$: 1,4-Piperazinediethanesulfonic acid (PIPES), for example, and combinations of two or more of the above.

An amount of buffer in the aqueous medium is that which is sufficient to promote release of nucleic acids from the non-rare cells but not from the rare cells. The amount of buffer in the aqueous medium is dependent on one or more of a number of factors such as, for example, the nature and amount of the sample, the nature of the buffer, the nature of the rare cells and the non-rare cells, the number of cells in the sample, the temperature and time of the holding of the sample and the aqueous medium, and the desired pH.

The phrase "nucleic acids" refers to polymeric macromolecules or polynucleotides formed from nucleotides and includes, but is not limited to, deoxyribonucleic acid (DNA) and ribonucleic acid (RNA), for example.

In accordance with the principles described herein, following incubation of the sample in the aqueous medium, the sample is treated to separate rare cells with intact nucleic acids from the non-rare cells in order to concentrate the number of rare cells versus the number of non-rare cells. In some examples, rare cells are also separated from released nucleic acids of the non-rare cells.

Prior to separation such as by filtration, the cells may be subjected to fixation, which immobilizes the cells and preserves cell structure. An amount of fixative employed is that which preserves the cells but does not lead to erroneous results in a subsequent analysis of target nucleic acids. The amount of fixative depends on one or more of the nature of the fixative and the nature of the cells, for example. In some examples, the amount of fixative is about 0.05% to about 0.15% or about 0.05% to about 0.10%, or about 0.10% to about 0.15%, for example, by volume of the sample. Agents for carrying out fixation of the cells include, but are not limited to, cross-linking agents such as, for example, an aldehyde reagent (such as, e.g., formaldehyde, glutaraldehyde, and paraformaldehyde,); an alcohol (such as, e.g., C1-C5 alcohols such as methanol, ethanol and isopropanol); a ketone (such as a C3-C5 ketone such as acetone); for example. The designations C1-C5 or C3-C5 refer to the number of carbon atoms in the alcohol or ketone. One or more washing steps may be carried out on the fixed cells using a buffered aqueous medium.

Separation of rare cells from non-rare cells may be achieved by, for example, filtration such as, but not limited to, capillary filtration, membrane filtration, microfluidic post filtration, and microfluidic membrane methods, for example. Filtration includes contacting the aqueous medium with a porous matrix. Any of a number of filtration techniques may be employed; such filtration techniques include, but are not limited to, microfiltration, ultrafiltration, or cross-flow filtration, for example. The porous matrix is generally part of a filtration module where the porous matrix is part of an assembly for convenient use during filtration.

In one approach the sample is contacted with a porous matrix such that rare cells are preferentially retained on the porous matrix and non-rare cells and released nucleic acids pass through the porous matrix.

The porous matrix is a solid or semi-solid material and may be comprised of an organic or inorganic, water insoluble material. The porous matrix can have any of a number of shapes such as, for example, tubular (e.g., hollow fiber, spiral wound, and hollow fine fiber), track-etched, or planar or flat surface (e.g., strip, disk, film, membrane, and plate). The matrix may be fabricated from a wide variety of materials, which may be naturally occurring or synthetic, polymeric or non-polymeric, fibrous or non-fibrous. The porous matrix can be produced by microelectromechanical (MEMS) technology, laser machining, metal oxide semiconductor (CMOS) technology or micro-manufacturing processes for producing microsieves. Examples, by way of illustration and not limitation, of such materials for fabricating a porous matrix include cellulose (including paper), nitrocellulose, cellulose acetate, polycarbonate, poly (vinyl chloride), polyacrylamide, polyacrylate, polyethylene, polypropylene, poly-(4-methylbutene), polystyrene, polymethacrylate, poly(ethylene terephthalate), nylon, and poly(vinyl butyrate), ceramic material, metallic material, for example, either used by themselves or in conjunction with one another and/or with other materials.

The size of the pores of the porous matrix is that which is sufficient to preferentially retain rare cells, which may be agglutinated, while allowing the passage of other materials such as released nucleic acids and non-rare cells through the pores in accordance with the principles described herein. The size of the pores of the porous matrix is dependent on the nature and size of the rare cells and the non-rare cells, whether the rare cells are agglutinated rare cells, the pressure applied to the blood sample, the degree of fixation, the capture particle size and nature of capture particle for example. In some examples the average size of the pores of the porous matrix is about 0.1 µm to about 100 µm, or about 1 µm to about 75 µm, or about 1 µm to about 50 µm, or about 1 µm to about 20 µm, or about 1 µm to about 10 µm, or about 5 µm to about 100 µm, or about 5 µm to about 75 µm, or about 5 µm to about 50 µm, or about 5 µm to about 20 µm, or about 5 µm to about 10 µm, for example. The density of pores in the porous matrix is about 1% to about 80%, or about 10% to about 80%, or about 20% to about 80%, or about 50% to about 80%, or about 20% to about 70%, for example.

As mentioned above, in some instances, nucleic acids may be a population of non-cellular nucleic acids. In such an instance, a capture particle entity is added that comprises a binding partner for the nucleic acids, which binds to the nucleic acids in the population of cellular nucleic acids to place them in particulate form for purposes of carrying out an enhancement of a concentration of nucleic acids over another population of nucleic acids to form a concentrated sample in accordance with principles described herein. The binding partner may be specific for nucleic acids in general or specific for one or more populations of nucleic acids or for a particular nucleic acid that may be present.

As mentioned above, some examples in accordance with the principles described herein are directed to methods of isolating and, optionally, determining circulating nucleic acids secreted from rare cells into a bodily fluid and free from cells. The fluid can further comprise non-rare cells. The sample is combined with an aqueous medium and a nucleic acid capture particle that can bind the nucleic acids. The combination is held for a period of time and at a temperature for selectively releasing nucleic acids from the non-rare cells but not from the capture particles. The sample is subjected to filtration to separate nucleic acids on the capture particle from other circulating components such as, for example, plasma, proteins, non-captured nucleic acids, lysed cells and small cells. The nucleic acids are removed from the nucleic acid capture particle and may further be identified.

The composition of the particle of the capture particle entity may be organic or inorganic, magnetic or non-magnetic with silica coating applied. Organic polymers include, by way of illustration and not limitation, nitrocellulose, cellulose acetate, poly(vinyl chloride), polyacrylamide, polyacrylate, polyethylene, polypropylene, poly(4-methylbutene), polystyrene, poly(methyl methacrylate), poly(hydroxyethyl methacrylate), poly(styrene/divinylbenzene), poly(styrene/acrylate), poly(ethylene terephthalate), melamine resin, nylon, poly(vinyl butyrate), for example, either used by themselves or in conjunction with other materials and including latex, microparticle and nanoparticle forms thereof. The particles may also comprise carbon (e.g., carbon nanotubes), metal (e.g., gold, silver, and iron, including metal oxides thereof), or colloids.

The diameter of the particles of the particle entity is dependent on one or more of the nature of the target nucleic acid, the nature of the sample, the nature and the pore size of a filtration matrix, the adhesion of the particle to matrix, the surface of the particle, the surface of the matrix, the liquid ionic strength, liquid surface tension and components in the liquid, and the number, size, and shape of the particles, for example. When a porous matrix is employed in filtration separation step, the diameter of the particles must be large enough to reduce background contribution to an acceptable level but not so large as to achieve inefficient separation of the particles from non-rare molecules. In some examples in accordance with the principles described herein, the average diameter of the particles should be at least about 0.02 microns (20 nm) and not more than about 2000 microns, or not more than about 250 microns. In some examples, the particles have an average diameter from about 0.1 microns to about 10 microns, or about 0.1 microns to about 15 microns, or about 10 microns to about 50 microns, or about 10 microns to about 100 microns, or about 50 micron to about 250 microns, or about 100 micron to about 300 microns, or about 200 to about 600 microns, or about 100 to about 600 microns, or about 600 to about 1500 microns, or about 600 to about 2000 microns, about 800 to about 1200 microns for example. In some examples, the adhesion of the particles to the surface is so strong that the particle diameter can be smaller than the pore size of the matrix. In other examples, the particles are sufficiently larger than the pore size of the matrix such that physically the particles cannot fall through the pores.

The capture particle includes a binding partner that is either specific or non-specific for the non-cellular target nucleic acid. The phrase "specific binding partner" refers to a molecule that is a member of a specific binding pair. A member of a specific binding pair is one of two different molecules having an area on the surface or in a cavity, which specifically binds to and is thereby defined as complementary with a particular spatial and polar organization of the other molecule. The members of the specific binding pair may be members of an immunological pair such silica, antibody, and polynucleotide pairs such as DNA-DNA, DNA-RNA, for example. On the other hand, non-specific binding involves non-covalent binding between molecules that is relatively independent of specific surface structures. Non-specific binding may result from several factors including hydrophobic interactions between molecules.

The binding partner may be bound, either covalently or non-covalently, to the particle of the particle reagent. "Non-covalently" means that the binding partner is bound to the particle as the result of one or more of hydrogen bonding, van der Waals forces, electrostatic forces, hydrophobic effects, physical entrapment in the particles, and charged interactions, for example. "Covalently" means that the binding partner is bound to the particle by a bond or a linking group, which may be aliphatic or aromatic and may comprise a chain of 2 to about 60 or more atoms that include carbon, oxygen, sulfur, nitrogen and phosphorus.

As mentioned above, in some embodiments, the combination is held for a period of time and at a temperature for selectively releasing nucleic acids from the non-rare cells but not from the capture particles. In some examples the temperature of the aqueous medium during the holding is about 5° C. to about 40° C., or about 5° C. to about 35° C., or about 5° C. to about 30° C., or about 5° C. to about 25° C., or about 5° C. to about 20° C., or about 5° C. to about 15° C., or about 10° C. to about 30° C., or about 10° C. to about 25° C., or about 10° C. to about 20° C., or about 20° C. to about 25° C., for example. The time period for the holding step is about 15 minutes to about 20 days, or about 15 minutes to about 15 days, or about 15 minutes to about 10 days, or about 15 minutes to about 7 days, or about 15 minutes to about 5 days, or about 1 day to about 20 days, or about 1 day to about 15 days, or about 1 day to about 10 days, or about 1 day to about 5 days, or about 2 days to about 20 days, or about 2 days to about 15 days, or about 2 days to about 10 days, or about 2 days to about 5 days, or about 5 days to about 10 days, or about 10 days to about 20 days, or about 10 days to about 15 days, for example.

In some examples in accordance with the principles described herein, pressure is applied to the sample on the porous matrix to facilitate passage of non-rare cells and altered released nucleic acids through the membrane. The term "pressure" refers to pressure differences from normal atmospheric pressure and can be either positive pressure (increase in pressure relative to normal atmospheric pressure) or negative pressure (vacuum) (decrease in pressure relative to normal atmospheric pressure). The level of pressure applied is dependent on one or more of the nature and size of the non-rare cells, the nature and size of the agglutinated rare cells, the nature of the porous matrix, and the size of the pores of the porous matrix, for example. In some examples, the level of positive pressure applied is about 1 millibar to about 500 millibar, or about 1 millibar to about 400 millibar, or about 1 millibar to about 300 millibar, or about 1 millibar to about 200 millibar, or about 1 millibar to about 100 millibar, or about 1 millibar to about 50 millibar, or about 1 millibar to about 30 millibar, or about 1 millibar to about 25 millibar, or about 1 millibar to about 20 millibar, or about 1 millibar to about 15 millibar, or about 1 millibar to about 10 millibar, or about 5 millibar to about 30 millibar, or about 5 millibar to about 25 millibar, or about 5 millibar to about 20 millibar, or about 5 millibar to about 15 millibar, or about 5 millibar to about 10 millibar, for example. The level of negative pressure (vacuum) applied is the negative of the above ranges.

In some examples the pressure applied to the sample on the porous matrix is an oscillating pressure, which means that the pressure is applied intermittently at regular or irregular intervals, which may be, for example, about 1 second to about 600 seconds, or about 1 second to about 500 seconds, or about 1 second to about 250 seconds, or about 1 second to about 100 seconds, or about 1 second to about 50 seconds, or about 10 seconds to about 600 seconds, or about 10 seconds to about 500 seconds, or about 10 seconds to about 250 seconds, or about 10 seconds to about 100 seconds, or about 10 seconds to about 50 seconds, or about 100 seconds to about 600 seconds, or about 100 seconds to about 500 seconds, or about 100 seconds to about 250 seconds, for example. In this approach, pressure is oscillated at about 0 millibar to about 10 millibar, or about 1 millibar to about 10 millibar, or about 1 millibar to about 7.5 millibar, or about 1 millibar to about 5.0 millibar, or about 1 millibar to about 2.5 millibar, for example, during some or all of the application of pressure to the blood sample. Oscillating pressure is achieved using an on-off switch, for example, and may be conducted automatically or manually. High pressure drops are allowable depending on one or more of reservoir volume, sample volume and filtration rate.

Contact of the sample with the porous matrix is continued for a period of time sufficient to achieve preferential detention of rare cells versus the non-rare cells on the porous matrix. The period of time is dependent on one or more of the nature and size of the non-rare cells, the nature and size of the rare cells whether or not agglutinated, the nature of the porous matrix, the size of the pores of the porous matrix, the level of pressure applied to the blood sample on the porous matrix, the volume to be filtered, the surface area of the filter, for example. In some examples, the period of contact is about 1 minute to about 1 hour, about 5 minutes to about 1 hour, or about 5 minutes to about 45 minutes, or about 5 minutes to about 30 minutes, or about 5 minutes to about 20 minutes, or about 5 minutes to about 10 minutes, or about 10 minutes to about 1 hour, or about 10 minutes to about 45 minutes, or about 10 minutes to about 30 minutes, or about 10 minutes to about 20 minutes, for example.

Nucleic acids that are retained on the surface of a membrane of a filtration device in accordance with the principles described herein may be removed by any convenient method. Examples of such methods include, but are not limited to, punching out the particle aggregate from the membrane into a suitable vessel, extraction of the particle aggregate from the membrane, filtering the carrier particles with label particles through the membrane, or by picking up carrier particles with label particles from the membrane, for example.

In the punch out approach, the membrane is cut into areas containing the cell or capture particle using an implement to segment or cut out the area. Such implements include, but are not limited to, a punch, a laser, and a cutting edge, for example. The area can be selected based on the presence of pores or by being pre-scribed for break-away. The area falls or is gathered into a well for treatment with liquids for washing, additional amplification or analysis of nucleic acids. Alternatively, the particle can be held by a magnetic force at the bottom of the well so they do not interfere with analysis.

Depending on a method for identification of nucleic acids of the rare cells as discussed in more detail hereinbelow, the sample may or may not be treated to extract nucleic acids from the rare cells. In the event extraction is carried out, a method employed for extraction of nucleic acids from the rare cells is dependent on the nature of the nucleic acids (e.g., DNA or RNA). Extraction of nucleic acids from the rare cells may involve one or more of the following processes: cell lysis; denaturation of DNA and proteins using denaturation agents such as, by way of illustration and not limitation, DNase and proteinase K, for example; removal of cellular membrane lipids; removal of cellular proteins; isolation of nucleic acids onto silica; sucrose gradient modification; spin column centrifugation; chromatography; magnetic particle separations such as, by way of example and not limitation, iron oxide beads coated with a layer of silica, for example; guanidinium acid-phenol extraction; treatment with chaotropic agents such as, but not limited to, guanidinium chloride and guanidinium isothiocyanate, for example; density gradient centrifugation using cesium chloride or cesium trifluoroacetate; use of glass fiber filters; lithium chloride and urea isolation; oligo(dt)-cellulose column chromatography; and non-column poly (A)+ purification/isolation nucleic acid purification, for example.

In examples in which fixation of the cells is employed, extraction of nucleic acids can include a procedure for defixation of the cells. Defixation may be accomplished employing, by way of illustration and not limitation, heat or chemicals capable of reversing cross-linking bonds, or a combination of both, for example.

Cell lysis involves disruption of the integrity of the cellular membrane with a lytic agent, thereby releasing intracellular contents of the cells. Numerous lytic agents are known in the art. Lytic agents that may be employed may be physical and/or chemical agents. Physical lytic agents include, blending, grinding, and sonication, and combinations or two or more thereof, for example. Chemical lytic agents include, but are not limited to, non-ionic detergents, anionic detergents, amphoteric detergents, low ionic strength aqueous solutions (hypotonic solutions), bacterial agents, and antibodies that cause complement dependent lysis, and combinations of two or more thereof, for example, and combinations or two or more of the above. Non-ionic detergents that may be employed as the lytic agent include both synthetic detergents and natural detergents.

The nature and amount or concentration of lytic agent employed depends on the nature of the cells, the nature of the cellular contents, the nature of the analysis to be carried out, and the nature of the lytic agent, for example. The amount of the lytic agent is at least sufficient to cause lysis of cells to release contents of the cells. In some examples the amount of the lytic agent is (percentages are by weight) about 0.0001% to about 0.5%, about 0.001% to about 0.4%, about 0.01% to about 0.3%, about 0.01% to about 0.2%, about 0.1% to about 0.3%, about 0.2% to about 0.5%, about 0.1% to about 0.2%, for example.

Removal of lipids may be carried out using, by way of illustration and not limitation, detergents, surfactants, solvents, and binding agents, and combinations of two or more of the above, for example, and combinations of two or more thereof. The use of a surfactant or a detergent as a lytic agent as discussed above accomplishes both cell lysis and removal of lipids. The amount of the agent for removing lipids is at least sufficient to remove at least about 50%, or at least about 60%, or at least about 70%, or at least about 80%, or at least about 90%, or at least about 95% of lipids from the cellular membrane. In some examples the amount of the lytic agent is (percentages by weight) about 0.0001% to about 0.5%, about 0.001% to about 0.4%, about 0.01% to about 0.3%, about 0.01% to about 0.2%, about 0.1% to about 0.3%, about 0.2% to about 0.5%, about 0.1% to about 0.2%, for example.

In some examples, it may be desirable to remove or denature proteins from the cells, which may be accomplished using a proteolytic agent such as, but not limited to, proteases, heat, acids, phenols, and guanidinium salts, and combinations of two or more thereof, for example. The amount of the proteolytic agent is at least sufficient to degrade at least about 50%, or at least about 60%, or at least about 70%, or at least about 80%, or at least about 90%, or at least about 95% of proteins in the cells. In some examples the amount of the lytic agent is (percentages by weight) about 0.0001% to about 0.5%, about 0.001% to about 0.4%, about 0.01% to about 0.3%, about 0.01% to about 0.2%, about 0.1% to about 0.3%, about 0.2% to about 0.5%, about 0.1% to about 0.2%, for example.

Methods employed for purifying nucleic acids from the rare cells are chosen based on the nature of the nucleic acids (DNA or RNA), for example. Purification of nucleic acids from the sample as treated above may be carried out using, by way of illustration and not limitation, alcohol precipitation (e.g., ethanol or isopropanol, or a combination thereof) or chloroform precipitation at a temperature of about −10° C. to about 10° C., phenol-chloroform extraction, minicolumn purification, affinity chromatography, and magnetic capture, and combinations of two or more thereof, for example.

The extracted nucleic acids also may be assessed for integrity. A method employed for integrity assessment is dependent on the nature of the nucleic acid (e.g., DNA or RNA), for example. Methods for assessment of nucleic acid integrity include, but are not limited to, agarose gel electrophoresis, spectrophotometric techniques (e.g., NANODROP® technology), and microfluidic techniques (e.g., such as, AGILENT 2100 BIOANALYZER), and combinations thereof, for example.

In some examples, different types of nucleic acids are separated from one another. For example, DNA and RNA may be separated from one another and from other cellular components such as, e.g., proteins, by methods that include, but are not limited to, differential centrifugation, solvent extraction combined with precipitation using salt, magnetic particle separation, and combinations thereof, for example.

Following extraction of the nucleic acids from the rare cells, the nucleic acids (target nucleic acids) are subjected to one or more identification techniques. In some examples, prior to, or in conjunction with, identification the nucleic acids may be subjected to a technique for amplifying nucleic acids. Such techniques include, but are not limited to, enzymatic amplification such as, for example, polymerase chain reaction (PCR), ligase chain reaction (LCR), nucleic acid sequence based amplification (NASBA), Q-β-replicase amplification, 3 SR (specific for RNA and similar to NASBA except that the RNAase-H activity is present in the reverse transcriptase), transcription mediated amplification (TMA) (similar to NASBA in utilizing two enzymes in a self-sustained sequence replication), whole genome amplification (WGA) with or without a secondary amplification such as, e.g., PCR, multiple displacement amplification (MDA) with or without a secondary amplification such as, e.g., PCR, whole transcriptome amplification (WTA) with or without a secondary amplification such as, e.g., PCR or reverse transcriptase PCR, for example.

Identification agents for identifying nucleic acids include, by way of illustration and not limitation, nucleic acid probes that have sequences complementary to sequences of nucleic acids (and are, therefore, specific for the complementary sequence), for example. The nucleic acid probe may be, or may be capable of being, labeled with a reporter group (label) or may be, or may be capable of becoming, bound to a support, or both. Binding of the probes to target nucleic acid sequences is detected by means of the labels. Binding can be detected by separating the bound probe from the free probe and detecting the label. In one example, a sandwich is formed comprised of the labeled probe, the target sequence and a probe that is or can become bound to a surface. Alternatively, binding can be detected by a change in the signal-producing properties of the label upon binding off the probe with the target sequence, such as a change in the emission efficiency of a fluorescent or chemiluminescent label. This permits detection to be carried out without a separation step. Detection of signal depends upon the nature of the label or reporter group. If the label or reporter group is an enzyme, additional members of the signal producing system include, for example, enzyme substrates. In one approach the target nucleic acids are immobilized on a solid support and then contacted with suitable labeled nucleic acid probes followed by detection of the labels.

The label is usually part of a signal producing system, which includes one or more components, at least one component being a detectable label, which generates a detectable signal that relates to the amount of bound and/or unbound label, i.e. the amount of label bound or not bound to the target nucleic acid being detected or to an agent that reflects the amount of the target nucleic acid to be detected. The label is any molecule that produces or can be induced to produce a signal, and may be, for example, a fluorescer, a radiolabel, an enzyme, a chemiluminescer or a photosensitizer. Thus, the signal is detected and/or measured by detecting enzyme activity, luminescence, light absorbance or radioactivity, depending on the nature of the label.

Suitable labels include, by way of illustration and not limitation, dyes; fluorescers, such as fluorescein, isothiocyanate, rhodamine compounds, phycoerythrin, phycocyanin, allophycocyanin, o-phthaldehyde, and fluorescamine; enzymes such as alkaline phosphatase, glucose-6-phosphate dehydrogenase ("G6PDH"), β-galatosidase, and horseradish peroxidase; ribozyme; a substrate for a replicase such as QB replicase; promoters; complexes such as those prepared from CdSe and ZnS present in semiconductor nanocrystals known as Quantum dots; chemiluminescers such as isoluminol and acridinium esters, for example; sensitizers; coenzymes; enzyme substrates; radiolabels such as $^{125}$I, $^{131}$I, $^{14}$C, $^{3}$H, $^{57}$Co and $^{75}$Se; particles such as latex enzyme substrates; radiolabels such as particles, carbon particles, metal particles including magnetic particles, e.g., chromium dioxide ($CrO_2$) particles, and the like; metal sol; crystallite; liposomes; cells, etc., which may be further labeled with a dye, catalyst or other detectable group.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances.

The label or other members of a signal producing system can be bound to a support or become bound to a molecule such as a cell that is disposed on a support. The support may be comprised of an organic or inorganic, solid or fluid, water insoluble material, which may be transparent or partially transparent. The support can have any of a number of shapes, such as particle, including bead, film, membrane, tube, well, strip, rod, planar surfaces (such as, e.g., sheet, plate and slide), and fiber, for example. Depending on the type of assay, the support may or may not be suspendable in the medium in which it is employed. Examples of suspendable supports are polymeric materials such as latex; lipid bilayers or liposomes; oil droplets, and metallic supports such as, e.g., magnetic particles; for example. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, and poly(vinyl butyrate), either used by themselves or in conjunction with other materials. In some examples, the support is the porous matrix used in a filtration as discussed above.

The label and/or other members of a signal producing system may be bound to a nucleic acid probe or another molecule. Bonding of the label to the probe may be accomplished by chemical reactions that result in replacing a hydrogen atom of the label with a bond to the probe or may include a linking group between the label and the probe. Other members of a signal producing system may also be bound covalently to nucleic acid probes. For example, two members of a signal producing system such as, for example, a fluorescer and quencher, can each be bound to a different nucleic acid probes that form a specific complex with a target nucleic acid. Formation of the complex brings the fluorescer and quencher in close proximity, thus permitting the quencher to interact with the fluorescer to produce a signal.

Subsequent to identification, the nucleic acids can be subjected to further analytic techniques such as, but not limited to, sequencing techniques, PCR, branched DNA testing, ligase chain reaction, and hybridization methods, including combinations of two or more of the above, for example. Methods of sequencing nucleic acids include, by way of illustration and not limitation, chemical sequencing (e.g., Maxam-Gilbert sequencing), chain termination sequencing (e.g., Sanger sequencing), de novo sequencing, shotgun sequencing, in vitro clonal amplification (e.g., bridge PCR), high throughput sequencing, sequencing by ligation (SOLiD sequencing), sequencing by synthesis, pyrosequencing, ion semiconductor sequencing, single molecule real-time sequencing, massively parallel signature sequencing (MPSS), Polony sequencing, DNA nanoball sequencing, single molecule sequencing, and combinations thereof, for example.

In some examples, in situ hybridization (ISH) techniques may be employed to identify nucleic acids that are present on or within a rare cell without extraction of the nucleic acids. ISH techniques utilize labeled nucleic acid probes that are complementary to the nucleic acids to be identified.

In some examples utilizing ISH techniques, it may be necessary to subject the rare cells to permeabilization. Permeabilization provides access through the cell membrane to nucleic acids of interest. The amount of permeabilization agent employed is that which disrupts the cell membrane and permits access to the nucleic acids. The amount of permeabilization agent depends on one or more of the nature of the permeabilization agent and the nature and amount of the rare cells, for example. In some examples, the amount of permeabilization agent by weight is about 0.1% to about 0.5%, or about 0.1% to about 0.4%, or about 0.1% to about 0.3%, or about 0.1% to about 0.2%, or about 0.2% to about 0.5%, or about 0.2% to about 0.4%, or about 0.2% to about 0.3%, for example. Agents for carrying out permeabilization of the rare cells include, but are not limited to, an alcohol (such as, e.g., C1-C5 alcohols such as methanol and ethanol); a ketone (such as a C3-C5 ketone such as acetone); a detergent (such as, e.g., saponin, Triton® X-100, and Tween®-20); for example. One or more washing steps may be carried out on the permeabilized cells using a buffered aqueous medium.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The following examples further describe the specific embodiments of the invention by way of illustration and not limitation and are intended to describe and not to limit the scope of the invention. Parts and percentages disclosed herein are by volume unless otherwise indicated.

EXAMPLES

All chemicals may be purchased from the Sigma-Aldrich Company (St. Louis Mo.) unless otherwise noted.
Abbreviations:
WBC=white blood cells
RBC=red blood cells
min=minute(s)
μm=micron(s)
mL=milliliter(s)
μL=microliter(s)
mg=milligrams(s)
μg=microgram(s)
mBar=millibar
RT=room temperature
DAPI=4',6-diamidino-2-phenylindole PBS=phosphate buffered saline (3.2 mM $Na_2HPO_4$, 0.5 mM $KH_2PO_4$, 1.3 mM KCl, 135 mM NaCl, pH 7.4)
EDTA=ethylenediaminetetraacetate Example 1. Separation of Rare Cell Nucleic Acids from Non-Rare Cell Nucleic Acids Whole blood specimens (about 8 mL) for testing were collected from healthy donors into tubes containing $K_3$EDTA and 0.45 ml TRANSFIX® preservative, which also contained 1% paraformaldehyde (VACUTEST® KIMA S. r. 1., Italy, TVT-09-50-45). Cancer cells were harvested from tissue culture and a known number added to each blood sample. The H226 or H2228 lung cancer cell line (ATCC) was used for testing. These unfixed cells were added at 1 to 10,000 cell counts per blood tube.

Buffer samples for testing were created by adding 9 mL of PBS plus 1% bovine serum albumin (BSA) to a tube containing $K_3$EDTA and 0.45 ml TRANSFIX® preservative, which also contained 1% paraformaldehyde (Vacutest® Kima S. r. 1. TVT-09-50-45). Cancer cells were harvested from tissue culture and a known number added to each tube. The H226 or H2228 lung cancer cell line (ATCC) was used for testing. These unfixed cells were added at 1 to 10,000 cell counts per tube.

Prior to filtration, a sample (7-10 mL) was transferred to a 50 mL FALCON® tube, which was filled to 20 mL with cold PBS or PBS with 0.2 to 10 mg/L fibrin added or with aqueous medium containing a buffer. The tubes were manually overturned twice. The mixtures were stored at 5° C. to 30° C. for 15 minutes to 7 days depending on the nature of the aqueous medium. The time and temperature were selected based on the absence of nucleic acids released from rare cells and the amount of nucleic acids released non-rare cells. The amount of nucleic acids released from rare and non-rare cells was determined by DAPI staining and microscopic examination. Nucleic acids liberated from cells were characterized as released.

The diluted sample was placed into a filtration station and the diluted sample was filtered through the membrane of the filtration station according to a method disclosed in U.S. Patent Application Publication No. 2012/0315664, the relevant portions of which are incorporated herein by reference. The membrane had an average pore size of 8 μm. During filtration, the sample on the membrane was subjected to a negative mBar, that is, a decrease greater than about −30 mBar from atmospheric pressure. The vacuum applied varied from 1 to −30 mBar as the volume of the sample was reduced during filtration. High pressure drops were allowable dependent on reservoir and sample volume and filtration rate. Following the filtration, the membrane was washed with PBS. The sample was not fixed with formaldehyde after filtration and was not subjected to permeabilization.

Following filtration, the membranes were either immediately processed to extract and purify RNA according to a method discussed below or were stored at −20° C. on pieces of tinfoil in plastic bags with desiccant. For testing, membranes containing filtered blood and spiked cancer cells were placed in a 1.5 mL Eppendorf tube and the membrane was pushed to the bottom of the tube using forceps. Proteinase K buffer was made by combining 240 μL of Buffer PKD (Qiagen mat #1034963, Qiagen, Inc., Valencia Calif.) and 10 μL of Proteinase K solution (Qiagen mat #1014023, Qiagen, Inc.). Proteinase K buffer (250 μL) was added to each membrane-containing tube. Proteinase K was used to release RNA from cells. The tubes were incubated at 56° C. for 15 min with occasional mixing by vortexing. The tubes were then incubated at 80° C. for 15 min with occasional vortexing. The tubes were held at room temperature while the heating block temperature was raised from 56° C. to 80° C. The higher temperature was employed to reverse formaldehyde crosslinking of the RNA.

Next, 500 μL of Buffer RBC (Qiagen mat #1034958, Qiagen, Inc.) was added to the Proteinase K buffer and membrane in the tube. The entire volume of the reaction mixture was loaded on a gDNA eliminator spin column (Qiagen mat #1030958, Qiagen, Inc.). This column, in combination with the high-salt buffer, was utilized to permit efficient removal of genomic DNA. The columns were spun at 8,000×g for 1 minute. The flow-through material was retained and the gDNA eliminator column was discarded. Then 1200 μL of 100% ethanol (Sigma E7023-4L) was added to the flow-through material. The flow-through material plus ethanol was passed through an RNEASY® mini spin column (Qiagen mat #11011708, Qiagen, Inc.) in batches of 700 μL at a time by spinning at 8,000×g for 1 min. Ethanol was added to the flow-through material from the gDNA Eliminator spin column to provide appropriate binding conditions for RNA, where the total RNA binds to the membrane and contaminants are efficiently washed away. The column was washed with 700 μL of buffer RW1 (Qiagen mat #1064143, Qiagen, Inc.) by centrifugation at 8,000×g for 1 min and the flow-through was discarded.

DNase solution was made by combining 26 μL water (Qiagen mat #1020506, Qiagen, Inc.), 4 μL DNase booster buffer (Qiagen mat #1064143, Qiagen, Inc.) and 10 μL DNase I (Qiagen mat #1064141, Qiagen, Inc.). DNase solution (40 μL) was added to each column, which were then incubated for 15 min at RT. Buffer RPE (Qiagen mat #1017974, Qiagen, Inc.) (500 μL) was added to each column and washed through by centrifugation at 8,000×g for 1 min. The flow-through material was discarded. Another 500 μL Buffer RPE was added to the column and washed through by centrifugation at 8,000×g for 1 min. The flow-through material was discarded. The columns were placed in new 2 mL collection tubes and spun at 20,800×g (centrifuge maximum speed) for 2 min to remove remaining traces of buffer. The flow-through material was discarded.

RNA was eluted from the columns by placing the columns into new 1.5 mL collection tubes and adding 30 μL RNAase free water directly to spin column (Qiagen mat #1017979, Qiagen, Inc.), then spinning the columns at 8,000×g for 1 min. Another 30 μL water was added to the columns and collected by centrifugation at 8,000×g for 1 min.

The purified RNA was immediately used in downstream applications or frozen at −20° C. or at −70° C. cDNA was synthesized using the ISCRIPT™ cDNA synthesis kit (Bio-Rad cat #170-8891, BioRad Laboratories, Inc., Hercules Calif.). 4 μL of 5×ISCRIPT™ reaction mixture, 1 μL of ISCRIPT™ reverse transcriptase, and 15 μL of template (isolated RNA) plus water were combined to form the cDNA reaction mixture. The cDNA reaction mixture was incubated in a thermal cycler (BioRad Laboratories, Inc.) in a thin walled tube on the following program: 1) 25° C. for 5 min, 2) 42° C. for 30 min, 3) 85° C. for 5 min, 4) 4° C. hold. As a control, reactions were prepared with and without reverse transcriptase. Samples with only water as the template were prepared as additional controls.

The target gene was amplified by PCR. Ten μL of HOT-STAR TAQ® Plus Master Mix (Qiagen mat #103962, Qiagen, Inc.), 1 μL of PRIMEPCR™ assay primers (BioRad Laboratories, Inc.), and 9 μL of template plus water was combined to form the PCR reaction mixture. 9 μL of the cDNA product was used as the template. The samples were incubated in a thermal cycler in thin walled tubes on the following program: 1) 95° C. for 5 min, 2) 94° C. for 1 min, 3) 60° C. for 1 min, 4) 72° C. for 1 min, 5) go to step 2 for 70 repeats, 6) 72° C. for 10 min, 7) 4° C. hold. As a control, a reaction with only water as the template was carried out.

The PCR products were detected by analysis on an Agilent 2100 Bioanalyzer (Agilent Technologies, Lake Forest Calif.) using the DNA 12000 kit or the DNA 1000 kit (Agilent Technologies). The presence of a band at the expected base pair size indicated that the original sample contained RNA of the target gene. The absence of a band in a corresponding sample where the cDNA reaction was carried out without reverse transcriptase indicated that the band is the result of detecting the target RNA and not a result of gDNA contamination.

Using the protocol described above, RNA was isolated from H2228 cells incubated in TRANSFIX® tubes with PBS buffer plus BSA, from H2228 cells spiked into blood from healthy donors in TRANSFIX® tubes, and from H226 cells spiked into blood from healthy donors in TRANSFIX® tubes. PRIMEPCR™ assay primers were used to detect both cytokeratin 19 (CK19), a cancer cell marker present in both cell lines, and anaplastic lymphoma kinase (ALK), a lung cancer subtype marker present in H2228 cells and absent in H226 cells. The results are shown below in Table 1 (+++ represents a strong band on the gel at a correct base pair (bp).

TABLE 1

| | ALK | | CK19 | | |
|---|---|---|---|---|---|
| Cells spiked | H2228 cells in aqueous medium | H2228 cells in blood sample | H2228 cells in aqueous medium | H2228 cells in blood sample | H226 cells in blood sample |
| 0 | 0 | 0 | 0 | 0 | 0 |
| 100 | +++ | 0 | +++ | 0 | +++ |
| 1,000 | +++ | +++ | +++ | +++ | +++ |
| 10,000 | +++ | +++ | +++ | +++ | +++ |

The above procedure was used on whole blood samples spiked with 100 to 100,000 H2228 cancer cells spiked except that the samples were not subjected to filtration. The manufacturer's method was followed for 8 mL of unfiltered whole blood samples (RNEASY® midi kit, Qiagen, Inc.). The method failed to detect the CK 19 and ALK RNA from H2228 even up to 100,000 cells/tube. Without being held to any particular theory, failure to detect the above cells might have been the result of contamination from genomic and circulating nucleic acids.

However, using a method in accordance with the principles described herein with filtration of the same blood sample diluted into aqueous medium, as few as 25 cells/tube were detected. This method was also effective to detect KRAS RNA form rare white blood cells in the sample. The detection of RNA can then be analyzed to investigate RNA expression levels in rare cells.

This result demonstrates that incubating the blood sample in an aqueous medium and subsequent filtration results in the detection of nucleic acids from rare cells. Table 1 above additionally shows that the sensitivity of the method to detect mRNA increases with incubation of the cells in an aqueous medium. In samples made entirely with aqueous medium, 100 cells were detected whereas, with samples made with diluted blood, the sensitivity was 1000 cells.

Images of blood samples with cancer cells treated in accordance with the principles described herein to alter the nucleic acids of the blood cells while leaving the nucleic acids of the cancer cells intact were compared. DNA of all the isolated cells was stained with DAPI. An anti-cytokeratin 8,18,19 stain was employed for cancer cells. The nucleus of the cancer cells retained a normal morphology while the nuclei of isolated rare white blood cells had highly abnormal nuclei indicating that treatment in accordance with the principles described herein selectively alters the nucleic acids of the white blood cells.

In addition, Agilent DNA gels (Agilent Technologies) were run using samples with and without reverse transcriptase (RT) and with and without cancer cells. PCR amplified cDNA was detected as a band only for samples containing cancer cells and RT.

Example 2. Separation of Circulating Rare Cell Nucleic Acids from Non-Rare Cell Nucleic Acid Whole blood specimens (about 8 mL) for testing were collected from healthy donors into tubes containing $K_3EDTA$ and 0.45 ml TRANSFIX® preservative, which also contained 1% paraformaldehyde (VACUTEST® KIMA S. r. 1. TVT-09-50-45). Cancer cells were harvested from tissue culture and a known number added to each blood sample. The SBKR cancer cell line (ATCC) was used for testing. These unfixed cells were lysed by sonication so that only cell free nucleic acids remains and added at 10^4(e.g. 10,000) to 10^8 cell counts per blood tube. Blood tubes were spun down using a centrifuge and plasma removed (about 3 to 5 mL). These plasma samples contained non rare cells (for example, peripheral blood mononuclear cells or buffy coat) in typical concentrations.

Prior to filtration, a plasma sample of (3-5 mL) was transferred to a 50 mL FALCON® tube, which was filled to 20 mL with cold PBS or aqueous medium containing buffer. This was followed by the addition of 25 μL of silica coated magnetic particles into each tube (Siemens Healthcare Diagnostics, VERSANT® Sample Preparation Reagents). This was followed by the addition of 25 μL of silica coated magnetic particles of 0.2 micron diameter into each tube (Siemens Healthcare Diagnostics, VERSANT® Tissue Preparation Reagents). Optionally, Proteinase K solution can be used to inactivate nucleases that might otherwise degrade the DNA or RNA during isolation.

The tubes were manually overturned twice. The mixtures were stored at 5° C. to 30° C. for 15 minutes to 7 days depending on the nature of the aqueous medium. The time and temperature were selected based on the amount of nucleic acids released from rare cells and separated by filtration from the nucleic acids on the capture particles. The amount of nucleic acids released from non-rare cells was determined by DAPI staining and microscopic examination.

The diluted sample was placed into a filtration station and the diluted sample was filtered through the membrane of the filtration station as shown in Example 1 with the only differences being that the filtration membrane pore sizes ranged from 0.1 μm to 10 μm and the vacuum applied varied from 1 to −80 mBar and the diameter of capture particle used was 0.2 μm. The sample was not fixed with formaldehyde after filtration and was not subjected to permeabilization.

Following the filtration, the membrane was incubated and washed with an aqueous media such as PBS or other buffer capable of releasing nucleic acids from non-rare cells, such as those containing buffered guanidine thiocyanate, ethanol, detergents and 0.05% proclin-300 (Siemens Healthcare Diagnostics, VERSANT® Sample Preparation Reagents). The buffer lyses cells and denatures nuclei while releasing RNA and DNA. The incubations and washes were done at 25° C. to 60° C. for 15 minutes to 2 hours depending on the nature of the aqueous medium. The number of washes, time of incubation, buffer and temperature were selected based on the absence of nucleic acids released from rare cells and non-rare cells. The amount of nucleic acids released from rare and non-rare cells was determined by DAPI staining and microscopic examination. Nucleic acids liberated from cells were characterized as released.

The membranes were either immediately processed to extract and purify nucleic acids according to a method as discussed in Example 1 or were stored at −20° C. on pieces of tinfoil in plastic bags with desiccant. In general, membranes, or portions thereof, were treated with an elution buffer such as 1M TRIS at pH 8.0 in a vial to extract the nucleic acids from the membrane. After elution, a DNase 1 digestion was done to remove DNA since only RNA analysis was needed.

Using the protocol described above, RNA was isolated from the lysed breast cancer SKBR cells spiked into blood from healthy donors in TRANSFIX® tubes. PRIMEPCR™ assay primers were used to detect the cytokeratin 19 (CK19) RNA from these lysed cells. The results are shown below in Table 2 (+++ represents a strong band on the gel at a correct base pair (bp).

TABLE 2

| Lysed dells spiked/mL | CK19 detected | |
| --- | --- | --- |
| | Particle treated with aqueous medium | Particle not treated with aqueous medium |
| 0 | 0 | 0 |
| 10^4 | ++ | 0 |
| 10^5 | +++ | + |
| 10^6 | +++ | ++ |

This result demonstrates that incubating the particles with aqueous medium and subsequent filtration results in the more sensitive detection of nucleic acids from rare cells. The sensitivity is the direct result of less non-rare cell RNA on the membrane. Table 2 above additionally shows that the sensitivity of the method to detect mRNA increases from 10^6 lysed cells to 10^4 lysed cells per mL of blood sample.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method of separating rare cells with intact nucleic acids from non-rare cells in a sample comprising the rare cells and non-rare cells, the method comprising:
   (a) combining the sample with an aqueous medium,
   (b) holding the combination for a period of time and at a temperature for selectively releasing nucleic acids from the non-rare cells but not from the rare cells, and
   (c) separating the rare cells from the sample by filtration, wherein the rare cells are cancer cells.

2. The method according to claim 1, wherein the combination is held for a period of about 15 minutes to about 20 days at a temperature of about 5° C. to about 30° C.

3. The method according to claim 1, wherein the sample is treated with a fixation agent prior to combining the sample with the aqueous medium.

4. The method according to claim 1, wherein the filtration comprises disposing the sample on a side of the porous matrix and applying pressure to the disposed sample.

5. The method according to claim 4, wherein the pressure applied is about 1 millibar to about 30 millibar and wherein the pore size of the porous matrix is about 0.1 μm to about 100 μm.

6. The method according to claim 1, further comprising extracting intact nucleic acids from the rare cells.

7. A method of isolating intact nucleic acids from rare cells in a sample comprising non-rare cells and circulating nucleic acids from rare cells, the method comprising:
   (a) combining the sample with an aqueous medium and nucleic acid capture particles,
   (b) holding the combination for a period of time and at a temperature for selectively releasing nucleic acids from the non-rare cells but not from the capture particles,
   (c) subjecting the medium to filtration to separate nucleic acids on the capture particles from non-rare cells, and
   (d) extracting intact nucleic acids from the capture particles.

8. The method according to claim 7, wherein the combination is held for a period of about 15 minutes to about 20 days at a temperature of about 5° C. to about 30° C.

9. The method according to claim 7, wherein the rare cells are cancer cells.

10. The method according to claim 7, wherein the filtration comprises disposing the sample on a side of the porous matrix and applying pressure to the disposed sample.

11. The method according to claim 10, wherein the pressure applied is about 1 millibar to about 30 millibar and wherein the pore size of the porous matrix is about 0.1 μm to about 100 μm.

12. A method of determining one or more nucleic acids in rare cells in a sample comprising the rare cells and non-rare cells, the method comprising:
   (a) combining the sample with an aqueous medium,
   (b) holding the combination for a period of time and at a temperature for selectively releasing nucleic acids from the non-rare cells but not from the rare cells,
   (c) separating the rare cells from the sample by filtration, and
   (d) identifying one or more of the nucleic acids of the rare cells,
   wherein the rare cells are cancer cells.

13. The method according to claim 12, wherein the combination is held for a period of about 15 minutes to about 20 days at a temperature of about 5° C. to about 30° C.

14. The method according to claim 12, wherein the sample is treated with a fixation agent prior to combining the sample with the aqueous medium.

15. The method according to claim 12, wherein the filtration comprises disposing the sample on a side of the porous matrix and applying pressure to the disposed sample.

16. The method according to claim 15, wherein the pressure applied is about 1 millibar to about 30 millibar and wherein the pore size of the porous matrix is about 0.1 µm to about 100 µm.

17. The method according to claim 12, wherein the identifying comprises contacting the nucleic acids with one or more identification agents specific for the one or more nucleic acids.

18. The method according to claim 12, wherein the nucleic acids are extracted from the rare cells and the extracted nucleic acids are subjected to one or more amplification techniques for amplifying nucleic acids.

* * * * *